(12) United States Patent
Heneine et al.

(10) Patent No.: US 6,596,478 B1
(45) Date of Patent: Jul. 22, 2003

(54) METHOD AND COMPOSITION TO DETECT C-TYPE RETROVIRAL INFECTION

(75) Inventors: Walid M. Heneine, Atlanta, GA (US); William M. Switzer, Stone Mountain, GA (US); Paul A. Sandstrom, Kanata (CA); Aprille L. Matthews, Charlottesville, VA (US); Thomas M. Folks, Snellville, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/720,218

(22) PCT Filed: Jun. 29, 1999

(86) PCT No.: PCT/US99/14662

§ 371 (c)(1),
(2), (4) Date: Mar. 12, 2001

(87) PCT Pub. No.: WO00/00829

PCT Pub. Date: Jan. 6, 2000

Related U.S. Application Data

(60) Provisional application No. 60/090,972, filed on Jun. 29, 1998.

(51) Int. Cl.$^7$ .......................... C12Q 1/70; G01N 33/53; A61K 39/395; A61K 39/21
(52) U.S. Cl. .................. 435/5; 435/7.1; 424/130.1; 424/147.1; 424/148.1; 424/184.1; 424/207.1; 424/208.1
(58) Field of Search ............... 424/130.1, 147.1, 424/148.1, 184.1, 207.1, 208.1; 435/5, 7.1

(56) References Cited

PUBLICATIONS

Wilson et al, Type C Retrovirus Released from Porcine Primary Peripheral Blood Mononuclear Cells Infects Human Cells, Journal of Virology, Apr. 1998, vol. 72, No. 4, pp. 3082–3087.*

Barbacid et al., Humans have antibodies capable or recognizing oncoviral glycoproteins, PNAS USA 77(3):1617–1621, 1980.*

Galbraith et al. "Design and validation of immunological tests for the detection of *Porcine endogenous retrovirus* in biological materials" *J. Virol. Methods* 90:115–124 (2000).

Matthews et al. "Development and validation of a Western immunoblot assay for detection of antibodies to porcine endogenous retrovirus" *Transplantation* 67(7):939–943 (1999).

Towbin "Western Blotting" *Encyclopedia of Immunology* 4:2503–2507 (1998).

Beaman "Nocardia, infection and immunity" *Encyclopedia of Immunology* 3:1861–1864 (1998).

Heneine et al. "No evidence of infection with the porcine endogenous retrovirus in human recipients of porcine islet cell xenografts" *Lancet* 352:695–699 (1998).

Groth et al. "Transplantation of porcine fetal pancreas to a diabetic patient" *Lancet* 344:1402–1404 (1994).

Tibell et al. "Morphological identification of porcine islet cells three weeks after transplantation into a diabetic patient" *Transplant Proc.* 26(3):1121 (1994).

Kaplan and Khabbaz "The epidemiology of human T lymphotrophic virus types I and II" *Rev. Med. Virol.* 3:137–148 (1993).

Schetters et al. "ELISA for the detection and quantification of C–type viral glycoprotein (gp70) using antibodies that recognize the protein moieties of the glycoproteins" *J. Virol. Methods* 2:357–366 (1981).

Erfle et al. "Time course of C–type retrovirus expression in mice submitted to osteosarcomagenic doses of Radium–224" *Int. J. Cancer* 26:107–113 (1980).

\* cited by examiner

*Primary Examiner*—Hankyel T. Park
*Assistant Examiner*—Stacy S. Brown
(74) *Attorney, Agent, or Firm*—Needle & Rosenberg, P.C.

(57) ABSTRACT

The present invention comprises methods, devices and compositions for detection of endogenous retroviruses found in xenotransplant materials. The methods and compositions are suited for detection of endogenous type-C retroviruses and in particular, for porcine endogenous retrovirus, PERV.

4 Claims, 5 Drawing Sheets

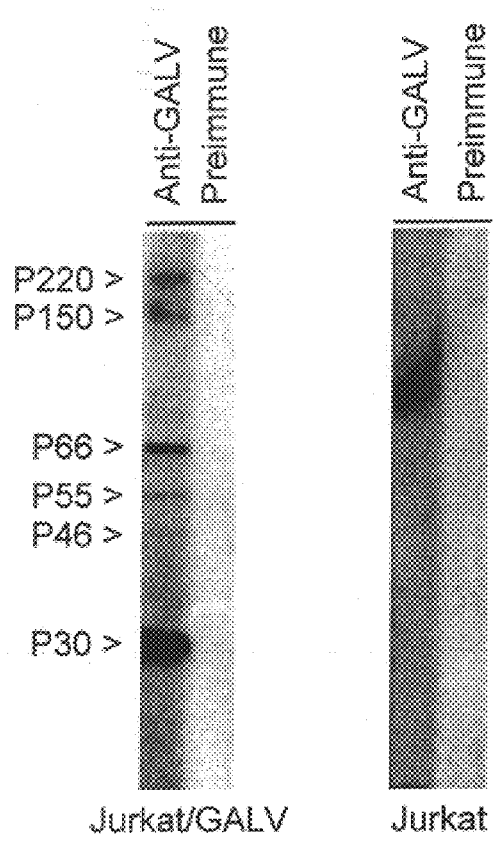
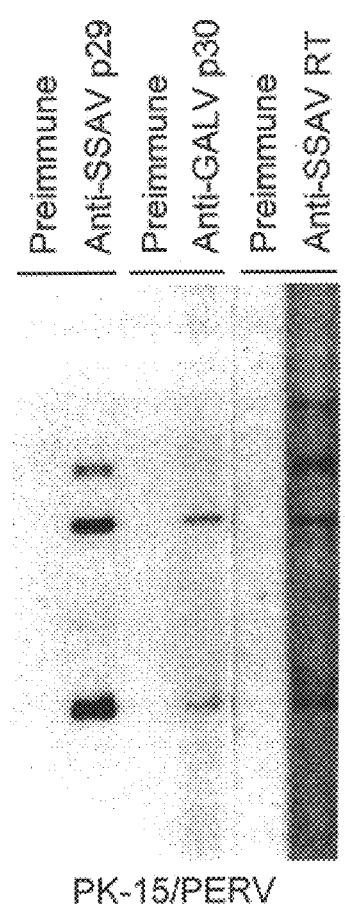
FIG. 1A
FIG. 1B

METHOD AND COMPOSITION TO DETECT C-TYPE RETROVIRAL INFECTION

PRIOR RELATED APPLICATIONS

This application is a 371 of PCT/US99/14662, filed Jun. 29, 1999, which claims the benefit of U.S. Provisional Application Ser. No. 60/090,972, filed Jun. 29, 1998, herein incorporated in its entirety.

This invention was made by the Centers for Disease Control, an agency of the United States Government.

TECHNICAL FIELD

The present invention relates to compositions, methods and devices for the detection of infection by endogenous retroviruses. In particular, the present invention comprises compositions, devices and methods for the detection of porcine endogenous retroviruses, detection of which is necessary following xenotransplantation of porcine cellular products.

BACKGROUND OF THE INVENTION

Currently, there are shortages of human organs and cells for transplantation into humans. These shortages of human donor material suitable for allotransplantation, coupled with recent advances in transplantation immunology, have provided impetus for attempts to develop xenotransplantation— the therapeutic use of living animal tissues and organs in humans.

To date, the therapeutic promise of xenotransplantation has not become widely accepted. There have been incidences of transplantation of simian organs and porcine cells and organs. Progress has been encouraging enough to merit the beginning of limited clinical trials in the United States.

Pigs are among the primary animal species proposed as sources of xenografts. Xenotransplantation clinical trials involving porcine tissue being considered or underway include, the perfusion through or implantation of whole liver preparations as a treatment for hepatic failure, the implantation of fetal neuronal tissue as a therapy for Parkinson's disease, and the infusion or implantation of pancreatic islet cells as a treatment for diabetes mellitus. Concerns have been raised that the implantation of porcine tissue and/or cells into immune compromised humans may facilitate the transmission of new infectious agents to humans. The Public Health Service has therefore stressed the importance of proceeding with xenotransplantation clinical trials only after there are diagnostic tools that detect infectious agents from pigs, surveillance programs for new xenograft recipients have been developed, and persons exposed to xenografts can be tested for evidence of infection.

There is such a need for detection and monitoring because porcine tissues and cells are infected with endogenous retroviruses. The genomes of all domesticated swine species tested thus far contain multiple integrated copies of an endogenous C-type retrovirus termed porcine endogenous retrovirus (PERV). Recently PERV has been reported to be transmissible to human cell lines in vitro, thus raising concerns that PERV may be capable of infecting recipients of porcine xenografts. The potential infection of human transplant recipients with new xenogeneic infectious agents, and subsequent transmission of these infections to the general population is a major concern when using animal tissue for human transplantation. Risks for xenogeneic infections may be significantly increased by the immunosuppressive therapies required to maintain graft function in human xenotransplant recipients.

One possible approach to detection of these xenogeneic infectious agents, including endogenous retroviruses, is to use molecular biological techniques. Recent sequence analysis of PERV genomes has allowed the development of diagnostic polymerase chain reactions (pcr) assays to monitor for the presence of virus in peripheral blood lymphocytes, sera or other tissues. However, these assays are limited to detecting infection when virus is present in the patient material sampled. An integrated copy of the PERV genome, that can be activated later within the human transplant recipient, cannot be detected except with PCR methods and then only if virus is present. Neither the potential for PERV to infect humans nor tissue tropism of PERV have been determined, and thus, it is not certain if human infection would be easily detectable by molecular approaches.

Prior to the present invention, there has been no development of a serologic assay that is capable of detecting PERV. The development of a specific serology assay has been problematic, due in part to a lack of an appropriate positive control antisera. Lack of antisera that only identifies PERV antigens, and not porcine or other cellular products has hampered advances in serologic detection methods.

Although immune sera from an animal infected with PERV would be ideal, cross-species infections by PERV have not yet been found. Pigs are immunologically tolerant to PERV and thus, do not make antibodies that are specific for viral antigens. Raising antisera by immunization with whole virus lysate would be a possible approach, however until very recently the only potential source of PERV antigens have been porcine cell lines constitutively expressing the virus. The preparation of viral proteins, free of contaminating porcine antigens, would be extremely difficult if not impossible to achieve from porcine-derived cells.

One method for stopping the transmission of porcine endogenous viruses from xenotransplantation would be to harvest the transplantation materials from virus-free animals. The risks of transmission of known infectious agents may be reduced, or eliminated by procuring source animals from specific pathogen-free colonies. However, this pretransplant screening method cannot eliminate the porcine endogenous retrovirus (PERV), because the genome of these viruses is carried in the germ line of every pig. Pig PERV particles of type C morphology are released spontaneously by cell lines originating from a variety of pig tissues including kidneys, lymph nodes, testes and fallopian tubes. All known PERVs originate from healthy porcine tissues except for two known. types, PERV-Shimozuma-1 and 38A-1 which are derived from porcine lymphomas.

The knowledge that PERV originating from both cell lines and primary porcine lymphocytes can infect human cells in vitro has heightened safety concerns related to pig xenografts. Transmission of xenogeneic retroviral infections to xenograft recipients is of particular concern because retroviruses are known to result in life long persistent infections. The current absence of the ability to detect the presence of PERV, which hampers the determination of whether PERV will infect humans exposed to porcine xenografts, and whether PERV will be transmitted secondarily among their contacts, has raised questions on the safety of pig-to-human transplantation, and threatens to delay progress in this therapeutic technology.

Thus, there is a long felt need for methods, devices and compositions that are capable of detecting the presence of endogenous viruses in transplantation materials or that may be released from implanted tissues. Particularly needed, are compositions and methods for diagnostic and monitoring assays that are capable of detecting the presence of antigens of endogenous viruses, particularly PERV antigens. Such assays would be important in providing vital diagnostic and physiologic information for xenotransplant recipients.

SUMMARY OF THE PRESENT INVENTION

In accordance with the present invention, compositions, methods and devices are provided that are effective in serologic detection of endogenous retroviruses. These methods and compositions are particularly effective in detecting type-C retroviruses, and more particularly are effective in detecting porcine endogenous retrovirus, PERV. These compositions and methods can be used in diagnostic devices for monitoring and detecting the presence of porcine endogenous retrovirus (PERV) in transplant recipients.

Accordingly, it is an object of the present invention to provide compositions that are capable of detecting type-C retroviruses.

It is yet another object of the present invention to provide methods and compositions for detecting type-C retroviruses.

Another object of the present invention to provide methods and compositions for serologic assays for detection of type-C retroviruses.

A further object of the present invention to provide compositions that are capable of detecting porcine endogenous retrovirus (PERV).

It is yet another object of the present invention to provide methods for detecting porcine endogenous retrovirus (PERV).

Another object of the present invention to provide serologic assay devices for detection of porcine endogenous retrovirus (PERV).

It is yet another object of the present invention to provide compositions, methods and devices for monitoring xenotransplant recipients for the presence of xenogeneic endogenous retroviruses.

It is an object of the present invention to provide compositions, methods and devices for detecting the presence of endogenous retroviruses in transplant material, including organs, tissues and cells.

Still another object of the present invention is to provide compositions, methods and devices for determining the zoonotic potential and tissue tropism of endogenous retroviruses.

These and other objects, features and advantages of the present invention will become apparent after a review of the following detailed description of the disclosed embodiments and the appended claims.

BRIEF DESCRIPTION OF THE DRAWINGS

FIG. 1 is a western immunoblot showing sera reactivity observed with goat anti-GALV antisera and lysates from Jurkat cells infected with GALV and uninfected Jurkat cells, or from PK-15 pig kidney cells expressing PERV.

DETAILED DESCRIPTION OF THE PRESENT INVENTION

Figure 2:
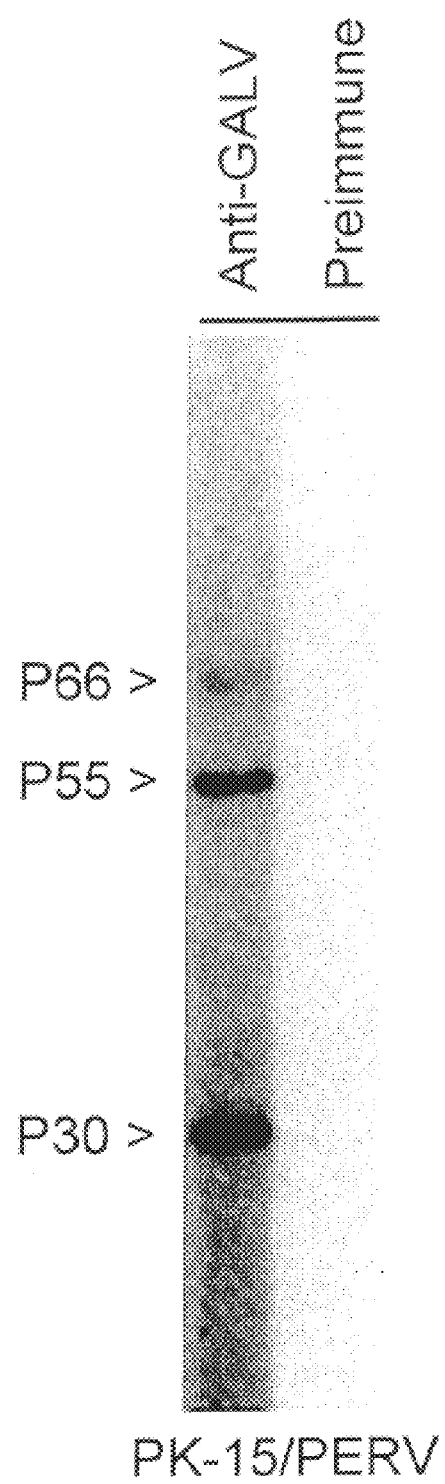
FIG. 2 is a western immunoblot showing sera reactivity observed with antisera specific for either GALV p30 or SSAV p29 cross-reacting with the 30, 55 and 66 kD proteins found in PK-15 pig kidney cells.

The present invention includes compositions, methods and devices for the detection of endogenous retroviruses, particularly type-C retroviruses, and more particularly, porcine endogenous retrovirus (PERV). The present invention also includes serologic assays that can be used for monitoring recipients of xenogeneic transplant materials.

Human transplant materials do not exist in the amounts necessary to meet the demands for transplantation. Therefore, other sources of transplant materials will be used. Such xenogeneic transplant sources may be infected with infectious agents, particularly viruses. Endogenous retroviruses rank as one of the types of infectious agents that are most worrisome for xenogeneic transplant recipients. The present invention is directed to providing compositions, methods and devices for surveillance of infection of transplant recipients by infectious agents delivered by the transplant materials.

One embodiment of the present invention comprises antigens that are specific for infectious agents. In particular, the present invention comprises virus antigens, more particularly endogenous C-type retrovirus antigens, most particularly antigens of porcine endogenous retrovirus, PERV. The present invention comprises compositions of such antigens, methods of use of such antigens and detection of such antigens, and serological assay devices employing such antigens.

The present invention also contemplates the methods of the present invention being used to detect and monitor endogenous retroviruses found in xenogeneic transplant materials. Such methods include determination of virus-specific antigens, free from contamination by antigens of the source animal. Antisera, specific for such viral antigens, may be polysera or monoclonal derived. Such antibodies may be produced by stimulated immune cells, either in vitro or in vivo, or by recombinant methods. Methods for producing such antibodies are known to those skilled in the art. Such antisera may be cross-reactive with antigens from related viruses.

Methods and compositions of the present invention include determination of viral antigens from endogenous viruses found in transplant materials using immunological methods. In particular, a preferred embodiment of the present invention comprises the determination of antigens that are specific for porcine, endogenous retrovirus, PERV, and use of serologic assays comprising such antigens to detect and monitor the presence of PERV in transplant recipients. The present invention contemplates the use of assays that have formats known to those skilled in the art. Such formats include, but are not limited to, ELISA, RIA, Western Blots, IFAs, and other formats known to those skilled in the art. The detection systems used in such assays include, but are not limited to radioactivity, enzymatic changes, colorimetric, fluorescent, chemi- and bioluminescence.

A preferred embodiment of the present invention comprises detection of PERV and monitoring of transplant recipients of porcine materials. Though the following description is directed to detection of PERV antigens and monitoring of porcine transplant recipients, it is an example of the methods of the present invention and can be thus applied to determination of other endogenous retroviruses of transplant materials, and is not limited to only PERV.

The present invention comprises methods of detecting infection by or immune exposure to mammalian C-type retroviruses by detecting antibodies to mammalian C-type retroviruses in immunoassay formats. Such formats include but are not limited to, Western blotting, ELISAs, IFA, RIA, sandwich assays, competitive assays, dipsticks, and other immunological determinative tests known to those skilled in the art. Detection is by reacting body samples from a human or animal containing antibodies with virus-specific antigens. Alternatively, body samples may be obtained and used as antigen sources so that the antigens are detected with antibodies known to react with such antigens.

The sample to be tested or analyzed may be obtained from any biological source and is preferably taken from a human or animal. For example, the sample may be a cell sample, tissue sample or biological fluid, such as whole blood, blood serum, blood plasma, urine, semen, saliva, sputum cerebrospinal fluid, lacrimal fluid, fermentation fluid, lymph fluid, tissue culture fluid, ascites fluid, synovial fluid, pleural fluid, and the like. The preferred biological sample is a biological fluid from which cells can be removed. The most preferred samples are blood plasma or serum. The biological sample may also be a laboratory research sample such as a cell culture supernatant, viral isolate or viral concentrate. The sample is collected or obtained using methods well known to those skilled in the art.

A preferred method comprises use of Western blotting techniques to determine the presence of antibodies to a type-C retrovirus. A most preferred embodiment comprises detection of antibodies to PERV.

Another embodiment of the present invention comprises monitoring recipients of xenografts for infection by zoonotic viruses. Serologic assays for the detection of antibodies to PERV are well suited to monitor recipients of porcine xenografts for PERV infection regardless of the tissue tropism of the virus. It is important that the serological assay does not detect porcine antigens, or that there is minimal seroreactivity because it is likely that porcine xenograft recipients will incur some degree of immune stimulation in response to porcine tissue itself.

Considerations of sensitivity and specificity are important when selecting the source of PERV target antigens used in a serology assay. In order to minimize potential background seroreactivity to irrelevant porcine antigens, it is optimal if the antigens were derived from non-porcine tissues. Of the estimated 50 integrated PERV genomes endogenous to all domesticated swine species, two (termed PERV-A and B) have been reported to infect human cells in vitro. It is also important that the antigen source be representative of those forms of PERV which are capable of directing the synthesis of fully infectious virions transmissible to human cell lines in vitro and therefore likely to be of greatest zoonotic potential.

The complete nucleotide sequence for PERV taken from the lymphocytes of miniature swine has recently been reported. The virus appears to have the highest degree of sequence homology to other mammalian C-type retroviruses, in particular gibbon ape leukemia virus (GALV) and murine leukemia virus (MuLV). Consistent with this genome relatedness, shared antigenic determinants on pol and gag encoded proteins have been demonstrated by competitive radioimmunoassays and inhibition of reverse transcriptase activity for a number of mammalian type C retroviruses.

One embodiment of the present invention comprises methods directed to the development and validation of a specific western immunoblot assay suitable for the diagnostic surveillance of porcine xenografts recipients for evidence of infection by PERV. This assay is based upon the cross-reactivity between simian type-C retrovirus specific antisera and several PERV encoded proteins found in infected human cells.

The PERV antigens, which are found on major structural proteins of the virus, were derived in vitro from human cells infected with PERV. The determination that these antigens were of PERV derivation was made using simian type-C retrovirus specific antisera. These antigens were electrophoresed and transferred to a substrate for use as a Western blot. With this Western blot format, the sera from recipients of porcine transplants can tested for antibodies specific for or reactive with, known PERV antigens. The strong cross-reactivity observed between structural proteins of simian C-type retroviruses and PERV allows the determination of PERV antigens and assays that are used for studies of PERV regulation, tissue specific expression and infectivity as well as the serologic screening of xenotransplantation animal models.

This embodiment of the serological assay of the present invention is based upon the cross-reactivity between antisera specific for the Gag encoded proteins of SSAV (simian sarcoma associated virus) and several PERV encoded proteins found in infected human cells. The strong serological response directed towards the Gag proteins of C-type retroviruses such as GALV (gibbon ape leukemia virus) and PERV is shown in FIG. 2. As this assay is based on PERV antigen derived from infected human cells, it has the capacity to detect a serological response towards PERV variants that have zoonotic potential. The use of PERV antigens derived from infected human cells as opposed to porcine tissue, also avoids possible complicating seroreactivities towards porcine antigens expected to be present in the circulation of individuals who receive porcine xenografts.

The assay for PERV was derived by the following techniques. Initial screening for reactivity to PERV by cross-reactive sera was performed against the PK-15 pig kidney cell line in an immunofluoresence assay format. This cell line contains approximately 50 PERV proviruses copies and has been shown to express PERV virions infectious for human cells in vitro. Based on reported sequence relatedness between PERV, GALV and MuLV (murine leukemia virus), initial screening was carried out using antisera raised against either lysed whole virus preparations of MuLV, GALV or the closely related SSAV. PK-15 cells stained with anti-GALV, SSAV and MuLV immune sera all demonstrated intense cytoplasmic fluorescence, while the corresponding preimmune antisera were negative, suggesting a specific antigenic cross reactivity between this group of viruses and PERV. Confirmation of cross reactivity and identification of the major cross reactive proteins found in PK-15 cell lysates was carried out by western immunoblot analysis. Anti-GALV sera and anti-SSAV sera reacted with a range of proteins in GALV-infected Jurkat cells (FIGS. 1 and 2). No reactivity was observed in uninfected Jurkat cells. These results define the major GALV proteins recognized by these reagents as having molecular weights of 30, 55, and 66 kD, both confirming the specificity of the antisera for simian C-type retroviruses as well as demonstrating the high degree of antigenic cross reactivity between GALV and SSAV.

Consistent with the IFA (immunofluoresence assay) results, antisera raised to a whole viral preparation of GALV reacted with three proteins in PK-15 cells corresponding to molecular weights of 30, 55 and 66 kD (FIG. 1). A preferred embodiment of the present invention comprises the detection of at least one of these antigens in a serological assay specific for PERV antigens. The present invention contemplates the detection of 1 to 3 of these antigens, of which any one of or all three of the 30, 55 and 66 kD proteins of PERV are detected. The molecular weights of these antigens are determined from placement in an electrophoresis gel as described herein and are approximately the weights shown, within experimental error.

The identity of these proteins was determined by cross reactivity with antisera raised against specific simian C-type retroviral proteins. The reported molecular weight for the processed Gag (core) proteins of mammalian C-type retroviruses is approximately 30 kD. Antisera specific for the major core proteins of either GALV or SSAV reacted with a 30 kD protein found in PK-15 cells, suggesting cross reactivity with the core protein of PERV (FIG. 2). The weaker reactivity observed at approximately 55 kD protein, based upon the predicted molecular weight and the expected conserved antigenicity, most likely represents the Gag precursor protein of PERV. It has been reported that unstimulated porcine peripheral blood lymphocytes do not express PERV. Unstimulated porcine PBL were negative for both supernatant RT activity as well as p30/p55 reactivity suggesting that the proteins being recognized in the PK-15 immunoblots were associated with PERV expression. The reactivity observed with antiwhole viral GALV at 66 kD is currently undefined. It is however unlikely to represent PERV reverse transcriptase as antisera raised against SSAV reverse transcriptase reacts with a protein of approximately 75 kD in PK-15 cells, suggesting that this reactivity is directed toward the reverse transcriptase enzyme of PERV predicted to have a molecular weight of 70 kD (FIG. 2).

Individuals who have received porcine islet cell xenografts as an experimental treatment for diabetes mount a serological response to porcine antigens. However, even in the absence of specific immune stimulation by porcine antigens, humans maintain a significant degree of seroreactivity towards the galactose-α-1-3-galactose (α-gal) terminal sugar residues found on porcine cells and porcine cell derived retroviruses. This glycoside epitope is absent in humans and Old World primates owing to frame-shift mutations in the galactose transferase gene. Persistent stimulation by α-gal on the surface of intestinal bacteria results in 1–2% of the circulating IgG in humans being specific for this glycoside. In order to minimize nonspecific cross-reactivity towards nonrelevant porcine antigens and α-gal glycoproteins, PERV derived from sources other than porcine tissue is required. PERV has been successfully passaged in several human cell lines including 293 human embryonic kidney cells providing a potential source of PERV antigens free of contaminating porcine antigens and α-gal glycoproteins.

Figure 3:
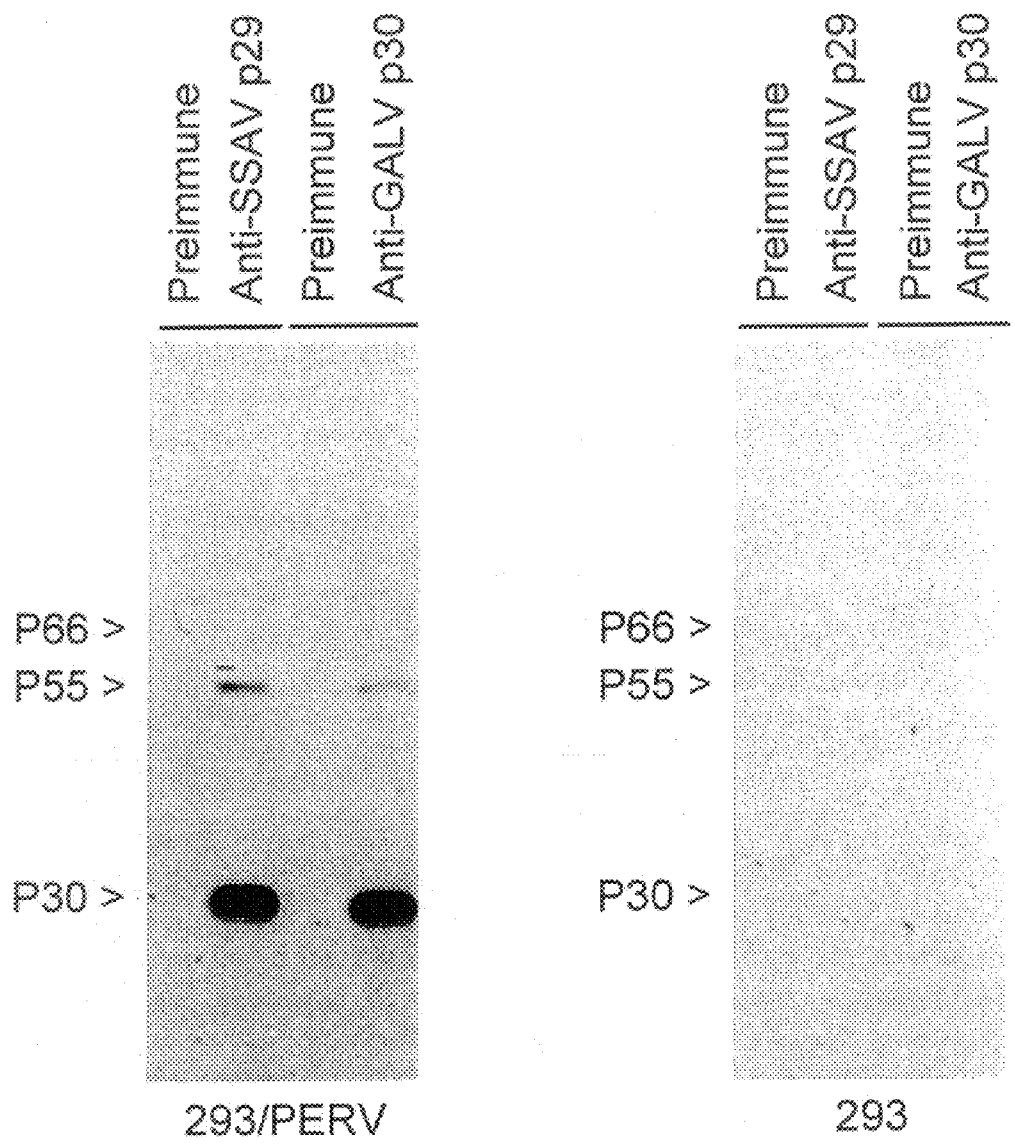
FIG. 3 is a western immunoblot showing sera reactivity observed with antisera specific for gag encoded proteins of either GALV or SSAV react with the processed and precursor forms of PERV Gag found in PERV infected 293 human, embryonic kidney cells. Corresponding preimmune sera were negative. No reactivity was observed with either immune or preimmune sera in uninfected 293 cells.

In order to confirm that the cross reactivity observed with anti-SSAV/GALV immune sera in PK-15 cells is PERV specific, as well as to further define assay conditions suitable for the screening of human porcine xenograft recipients, antisera was tested against both PERV-infected 293 cells as well as uninfected 293 cells as a control for seroreactivity toward cellular proteins. The pattern of cross reactivity observed with antisera directed toward the core antigens of simian C-type retroviruses in preparation of PERV infected 293 cells was identical to that observed with PK-15 cells (FIG. 3). Uninfected 293 cells were negative for both preimmune and immune antisera suggesting that the observed cross reactivity seen is directed towards PERV Gag antigens and is not non specific seroreactivity with cellular proteins. Western immunoblot results were confirmed by IFA.

Figure 4:
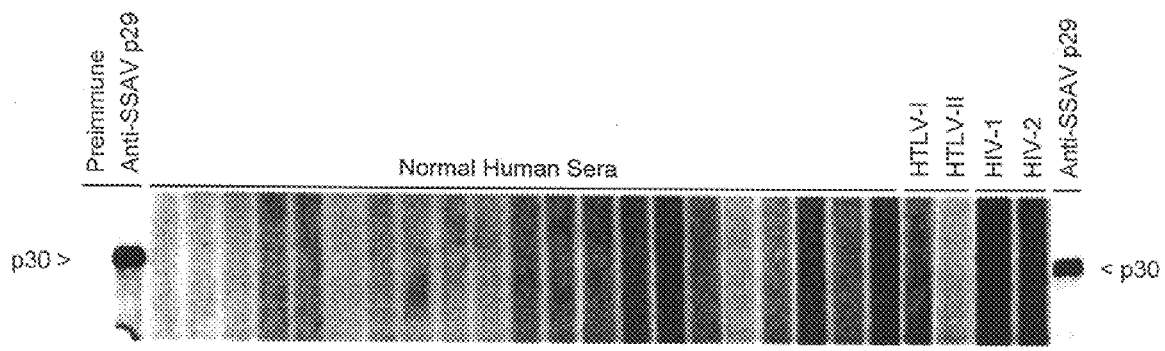
FIG. 4 is a western immunoblot showing the nonreactivity of sera from normal or HTLV-1, HTLV-II, HIV-1 or HIV-2 infected humans to PERV p30 antigen.

In preliminary screening for western blot reactivity to PERV p30 in 200 U.S. blood donors, including normal or HTLV-I, HTLV-II, HIV-1 or HIV-2 infected humans (FIG. 4), no positive results have been identified (FIG. 4). The observed absence of western blot reactivity in this sample population shows the utility of this assay in the proposed surveillance of porcine xenograft recipients. Cross reactivity between PERV gag encoded proteins and antibodies directed toward human lentiviruses or oncoretroviruses would potentially complicate the interpretation of this assay. In particular human C-type retroviruses such as HTLV-I and HTLV-II demonstrate sequence relatedness to other mammalian C type retroviruses. In order to exclude the possibility of false positives due to cross reactivity in sera from HIV and HTLV infected individuals, control sera known to be strongly reactive to HIV-1, HIV-2, HTLV-I or HTLV-II were tested by western immunoblot against PERV infected 293 cells. Numbers of control sera from the following groups were tested: 58 with immunodeficiency virus-1, 18 with human immunodeficiency virus-2, 13 with human T-cell lymphotrophic virus-I, and 21 with human T-cell lymphotrophic virus-II. Additionally, 15 cytomegalovirus-positive sera samples tested negative for PERV p30 reactvivity. No reactivity was observed in the sera from any of these patient groups, strongly suggesting that false positives attributable to cross reactivity with known human retroviruses is very unlikely (FIG. 4). In one method for surveillance of transplant recipients, multiple sera samples are taken at various time points before and after xenograft exposure to will allow for the identification of potential seroconversion rather than simply seropositvity, providing strong evidence of xenotransplantation associated exposure to PERV. This method further diminishes the possibility of false positive results in the assay.

Monitoring and Surveillance of Human Recipients of Porcine Transplant Material

Ten patients (mean age 40 yrs) with long-standing insulin dependent diabetes (mean duration 30 years) and end-stage diabetic nephropathy underwent transplantation with fetal porcine pancreatic islet-like cell clusters (ICC) between June 1990 and April 1993. Patients were given between 200,000–1,000,000 ICC, which represent around $4 \times 10^8$ to $2 \times 10^9$ cells based on an estimate of 2,000 cells per ICC. The first eight patients had undergone renal transplantation 2–7 years earlier; all eight were given the ICCs by intraportal injection. Two other patients received the ICCs under the capsule of a simultaneously transplanted kidney graft. Cyclosporine, prednisolone, and azathioprine was used for maintenance immunosuppression in 9 patients, while one patient received prednisolone and azathioprine only. At the time of the xenoislet transplantation, five patients were given adjunctive immunosuppressive treatment with rabbitantithymocyte globulin while 5 other patients were given 15-deoxyspergualin.

Evidence of survival of the porcine cells in patients previously found included detection of low levels of porcine C-peptide in urine in 4 patients lasting until 250 to 450 days after islet transplantation. A renal biopsy obtained 3 weeks after transplantation from a fifth patient (XJT10) who received ICC under the renal capsule revealed clusters of epithelial cells which stained positively for insulin, glucagon and chromogranin, demonstrating cell viability and ability to produce insulin.

All patients have been followed up regularly during the 4.5–7.5 years after xenoislet transplantation. During the first year no patient was hospitalized for febrile disease. Subsequently, one patient who was suffering from chronic asthma was hospitalized several times for pneumonia. Six patients have been treated for infectious diabetic ulcers with concomitant local infections. Also, there have been several instances of lower urinary tract infections, and one patient was treated for Klebsiella septicemia 4 years after transplantation. Two patients (XIT2 and MT 10) died of myocardial infarction 2.5 and 5 years after the xenotransplantation. One patient (XIT4) lost a renal graft in chronic rejection. This event occurred 12 years after the renal transplantation, and six years after the xenoislet transplantation. The mortality and morbidity was not different than that seen in diabetic renal transplant recipients. None of the patients had signs of lymphoproliferative disease or neurological disease of the kind associated with C-type retroviruses in humans or animals. See Groth C. G. et al., "Transplantation of porcine fetal pancreas to diabetic patients", Lancet 344: 1402–144 (1994); Tibell, A. et al., "Morphological identification of porcine islet cells three weeks after transplantation to a diabetic patient", Transplant Proc. 26:1121 (1994); Kaplan, J. E. and Khabbaz, R. F., "The epidemiology of human T lymphotrophic virus types I and II", Rev. Med. Virol. 3:137–148 (1993).

In Heneine, W., Tibell, A, Switzer, W M et al., "No evidence of infection with the porcine endogenous retrovirus in human recipients of porcine islet cell xenografts." Lancet, 1998. 352:695, is reported the results of using the present invention. This reference is herein incorporated by reference in its entirety. Although prolonged xenograft survival and increased titers of anti-porcine antibodies were documented in this group of patients, Western blot analysis for antibodies to PERV supported absence of infection in all patients. Interestingly, a weak p30 reactivity was seen in 7 samples from one patient collected from day 3 to 6.8 years after xenografting. These results do not represent a seroconversion to p30 and are not associated with the xenograft exposure. The inability to detect any PERV sequences in this patient supports absence of preexisting PERV infection and suggests that the observed weak reactivity is nonspecific.

The risks of cross-species transmission of PERV to these patients following exposure to pig xenografts was investigated using molecular biological techniques and the compositions and methods of the present invention. Markers of persistent PERV infection in these patients were looked for including evidence of anti-PERV antibodies. Testing by serologic methods at multiple time points after transplantation revealed no evidence of PERV in any patient. The negative serologic results are not due to a compromised humoral immunity by the immunosuppressive therapy, since all patients demonstrated immunocompetence by developing antipig antibodies within weeks after transplantation. Thus, using the compositions and methods of the present invention, the infection status of these patients can be followed, and in the case of these patients, there was an absence of PERV infection in these patients.

The lack of transmission of PERV to these patients was an unpredicted outcome because of several factors that would be expected to facilitate infection with PERV. First, PERV is known to be able to infect human cells. Second, evidence of extended persistence of the pig cells, which all harbor potentially infectious provirus, was documented in 5 patients by functional, morphologic, and molecular methods. Third, all patients received chronic immunosuppressive therapy. The reasons PERV failed to infect these patients are not clear but are not likely due to the rapid clearance of porcine cells. Both molecular and functional evidence of extended survival of pig cells has been found in these patients. Evidence of excretion of porcine Cpeptide by 4 patients up to 450 days after the transplantation argues for extended graft survival.

Tests of patient sera was done to look for evidence of abortive or transient early infections using the compositions and methods of the present invention. No antibody seroconversion to PERV gag proteins 6 months after the xenotransplants was detected. The potential for exposure to PERV from the xenograft may be highest during the first month following the transplant. Viremias following exposures, to other retroviruses (HIV-1 or simian immunodeficiency virus) are commonly seen during this time interval.

These particular laboratory investigations show the utility and necessity for the use of the methods and compositions of the present invention. In these particular patients, a small sample, no evidence was found to support either transient or persistent infection with PERV in any patient studied. To date, none of the patients have presented with unexpected clinical illness or developed malignant or neurologic diseases characteristic of C-type retrovirus infections in man or other mammals. The methods and compositions of the present invention can be used to both detect the presence of endogenous viruses and to monitor patients who have received xenotransplants potentially carrying exogenous retroviruses.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I
Development of the Western Blot

PK-15 and Jurkat cells were obtained from the Biological Products Branch at the Centers for Disease Control and Prevention. PERV-infected 293 human embryonic kidney cells and uninfected 293 kidney cells were a generous gift from Robin Weiss (London, UK). The antisera used for assay development were generated at the National Institute of Health and archived by Quality Biotech (Camden, N.J., U.S.A.). All antisera used was raised in goats immunized with either Tween either-disrupted whole viral preparations or with chromatography-purified viral proteins. The anti-SSAV p29 protein reagent eventually selected as the postive control for the assay was raised in a goat by intracutaneous immunization with ion exchange chromatography.

Cells were washed once with PBS and mounted on a multi-chamber adhesion slide (Merifeild, Germany). After acetone fixation, cells were reacted with either a 1:25 or 1:50 dilution of immune or preimmune sera for 30 minutes followed by a 1:200 dilution of a FITC conjugated anti-goat immunoglobulin secondary reagent. Cells were visualized on a Nikon Axiophot fluorescence microscope.

PERV-infected or noninfected whole cell lysates (150 $\mu$g total protein) were electrophoresed for 2 hours at 70 volts on precast preparative SDS/TRIS/HCl polyacrylamide gels (BioRad, Hercules Calif.). Antigens were transferred to PVDF (polyvinylidene difluoride) membranes by electroblotting followed by blocking over night in 5% non fat dried milk. The membranes were then reacted with test sera using a miniblotter 205L (Immunetics, Cambridge Mass.), allowing for the simultaneous screening of individual sera for immunoreactivity against proteins in either PERV-infected or non-infected control cell lysates. Blots were reacted for 3 hour at a 1:100 dilution of antisera followed by a 1:7,000 dilution of protein A/G horse radish peroxidase (Pierce, Buckinghamshire, UK) for 1.5 hours. Blots were visualized by chemiluminescence using ECL western blot detection reagent (Amersham, Rockford Ill.) and exposing for 10 to 15 seconds on hyperfilm ECL (Amersham).

EXAMPLE II
Serologic Screening for Antibodies to PERV

Sera were tested for PERV antibodies by a Western immunoblot assay. Whole cell lysates derived from human kidney 293 cells infected with PERV-PKI5 (kindly provided. by Robin A. Weiss) were used as a source of PERV antigen. Blots were reacted for 3 hours at either 1:50 dilution of patient sera, or a 1:100 dilution of control antisera followed by a 1:7,000 dilution of protein AIG horse radish peroxidase (Pierce, Buckinghamshire, England) for 1.5 hours. Blots were visualized by chemiluminescence using ECL western blotting reagents (Amersham, Rockford, Ill., USA). Based on the reported cross-reactivity between the gag antigens of PERV and simian sarcoma associated virus (SSAV, a retrovirus that is highly related to the gibbon ape leukemia virus), a goat anti-SSAV p29 antiserum was used as a positive control antiserum. This antiserum shows strong reactivity to the PERV p30 found in 293 PERV-PK cells, and no reactivity to uninfected 293 cells.

Figure 5:
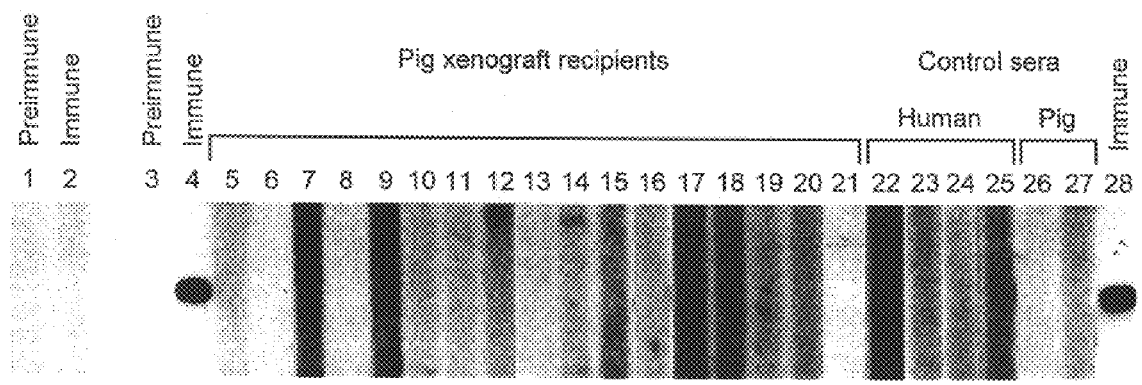
FIG. 5 is a western immunoblot of antibodies to PERV in porcine xenograft recipients, nontransplant human controls and pigs.

Antibodies to p30 PERV protein were not detected in any serum sample collected around 6 months post transplantation from 10 patients. Additional serum samples collected from 8 patients from two time points between 4 and 7 years after transplantation were also found to be seronegative. Representative results are shown in FIG. 5. These results demonstrate persistent seronegativity to PERV p30 proteins. Sera from 2 pigs also tested negative confirming immunologic tolerance to PERV proteins, as expected with an endogenous virus.

In FIG. 5, Lanes 1 and 2 are blots from uninfected 293 human kidney cells reacted with preimmune serum and goat anti-p29 protein of simian sarcoma associated virus (SSAV) serum, respectively. All other lanes represent blots from PERV-infected 293 human kidney cells reacted with: lane 3, preimmune control serum; lane 4 and 28, anti-SSAV p29 immune serum; lanes 5 through 21, sera from porcine xenbgraft recipients taken 4 to 7 years post transplant; lanes 22–25, control sera from unexposed human blood donors; lanes 26 and 27, pig control sera.

EXAMPLE 3

In a study investigating the possible cross species transmission of porcine endogenous retrovirus (PERV), 160 patients were treated with various living pig tissues from 1 day to over 12 years prior to the testing. In addition to nucleic acid testing, Western blot analyses for the presence of anti-PERV antibodies were performed. Persistent microchimerism was demonstrated in 23 patients for up to 8.5 years. No PERV infection was detected in any of these patients. These results were submitted to Science, to be published in 1999. This reference is herein incorporated in its entirety.

Study Participants and Testing Laboratories

One hundred and sixty patients (83 males, 77 females; aged 2–77 years) participated in this study. The patients had previously been treated using one of the following procedures: (a) Extracorporeal splenic perfusion. (ECSP) (n=100) through spleens from healthy slaughterhouse pigs as "immunotherapy" for various indications. One patient subsequently received chemotherapy; (b) Extracorporeal perfusion for liver failure using the HepatAssist device (n=28), which contains pig hepatocytes enclosed in a semi-permeable membrane.

After the procedure, 26 of these patients received pharmacological imnnunosuppression following a liver allotransplant. (c) Pig skin grafts (n=15) for burns; (d) Porcine pancreatic islet cell transplants for diabetes (n=14). Eight of these patients also received a kidney allotransplant and nine pharmacological immunosuppression. Evidence of porcine C peptide (released from islets) was detected in the urine of 4 patients for 257 to 460 days; (e) Extracorporeal pig kidney perfusion (n=2); (f) Extracorporeal perfusion through a whole pig liver (n=1) followed by a liver allotransplant and pharmacological inmunosuppression.

Four laboratories conducted testing designed to detect infectious states described for feline leukemia virus (FeLV), a closely related C-type retrovirus (latent, persistent, sequestered and cleared or "recovered"). The testing sites used different primers, antigens, and methodologies in their respective assays.

Detection of anti-PERV antibodies. At one testing site, a recombinant PERV p30 Gag protein (expressed in *Escherichia coli*) was used as an initial anti-PERV antibody screen, and positive samples were then tested against the purified whole virus (isolated from a PERV positive human cell line), using the methods of the present invention. A sample was considered to be positive when it reacted against p30 Gag antigen in both assays.

At CDC, reactivity to Gag and p27 were measured in the methods of the present invention by using whole cell lysates prepared from PERV-infected human 293 cells.

No anti-PERV antibodies were detected in 156/160 patients at either laboratory. Seroreactivity was detected in two patient samples (6062, 6052) when tested at the first site; one of these (6052) had a weak signal and tested negative 7 months later. However, all these samples were found to be seronegative by CDC, using any combination of the first site and CDC antigens and methods. The five close contacts of these 2 patients were seronegative when tested at the first site.

A weak seroreactivity was detected in two patient samples (10018, 8004) only when tested at CDC. Similar reactivity was present in serum samples obtained 1 and 3 days after their respective procedures, suggesting pre-existing antibodies rather than seroconversion.

None of the 4 seroreactive patients from either laboratory had molecular evidence that would support PERV infection.

Summary and Interpretation

No evidence of persistent PERV infection was detected in any of the 160 patients in this study, including 37 who were pharmacologically immunosuppressed and therefore presumed to be at increased risk of infection.

The absence of identifiable adverse events in any of the 23 patients with identified microchimerism, despite 43.7 person years of cumulative exposure to pig cells, was reassuring. Despite prolonged presence of pig cells in the circulation in at least 23 of the study patients, no evidence of productive infection was detected by testing either serum (160 patients) or saliva (16 microchimeric patients). These observations were very encouraging as the development of disease and transmission of viruses related to PEV, like FeLV, are usually associated with a persistent plasma viremia and widespread replication of the virus in epithelial cells, hematopoietic cells and other tissues.

Only 2/160 patients were seroreactive at the first testing site, neither of whom had available preprocedural serum. Both were seronegative at CDC, and a substantial effort was made to resolve these differences. The discrepant results were not antigen dependent, but more likely were due to technical differences between the two methodologies. It is not yet possible to determine if the antibody response seen at the first site represents an immunological response to PERV protein or if it was due to cross-reactivity with an unrelated antigen. Cross-reactive antibodies to retroviral gag proteins have previously been described. All other molecular tests (PCR, RT-PCR in serum and saliva) in these patients were negative, and the close contacts of these patients were also found to be negative for PERV by PCR, as well as seronegative by Western blot.

In conclusion, in this large, multicenter study of 160 patients treated with porcine living tissue, using state of the art analytical techniques at multiple testing sites, there was no conclusive evidence of cross species or human-to-human transmission of PERV. Thus, the present invention is an important tool in detecting the presence of PERV and monitoring the status of patients with xenotransplants.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of detecting zoonotic infection in a xenograft recipient, comprising:

a) reacting a body sample from the xenograft recipient with an antigen of a C-type retrovirus under conditions whereby an antigen/antibody complex could form; and b) detecting formation of an antigen/antibody complex, thereby detecting zoonotic infection in the xenograft recipient, wherein the antigen is not a glycoprotein.

2. The method of claim 1, wherein the body sample is blood, serum, saliva, or tears.

3. The method of claim 1, wherein detecting formation of an antigen/antibody complex is carried out by Western blotting.

4. The method of claim 1, wherein the antigen is a porcine endogenous retrovirus antigen.

* * * * *